(12) United States Patent
Shibasaki et al.

(10) Patent No.: US 6,833,442 B2
(45) Date of Patent: Dec. 21, 2004

(54) COMPLEX AND METHOD FOR PRODUCING EPOXIDES BY USING THE COMPLEX

(75) Inventors: Masakatsu Shibasaki, Mitaka (JP); Takashi Ohshima, Tokyo (JP); Tetsuhiro Nemoto, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 10/211,548

(22) Filed: Aug. 5, 2002

(65) Prior Publication Data
US 2003/0130488 A1 Jul. 10, 2003

(30) Foreign Application Priority Data
Aug. 9, 2001 (JP) ........................................ 2001-241553

(51) Int. Cl.⁷ ................................................. C07F 5/00
(52) U.S. Cl. ......................... 534/15; 526/906; 526/915; 528/88; 502/100; 523/400
(58) Field of Search ............................ 534/15; 549/512; 502/100; 526/915, 906; 528/87, 88; 523/400, 423

(56) References Cited

PUBLICATIONS

Nemoto et al (Feb. 28, 2001), J. Am. Chem. Soc., vol. 123, No. 12, pp. 2725–2732.*

* cited by examiner

*Primary Examiner*—Dameron L. Jones
(74) *Attorney, Agent, or Firm*—Oliff & Berridge, PLC

(57) ABSTRACT

There is provided a complex having a specified chemical structure and an asymmetric catalyst using such a complex. Further, an epoxidation of amine or ketone is enantioselectively conducted by using such an asymmetric catalyst.

6 Claims, 4 Drawing Sheets

COMPLEX AND METHOD FOR PRODUCING EPOXIDES BY USING THE COMPLEX

BACKGROUND OF THE INVENTION

1. Field of the Invention

This invention relates to a complex and an asymmetric catalyst using such a complex, and more particularly to an asymmetric catalyst high-enantioselectively promoting an epoxidation reaction of an amide or a ketone. Furthermore, the invention relates to a method for producing epoxides by using the asymmetric catalyst.

2. Description of Related Art

The epoxidation means a reaction for oxidatively changing an alkene to an epoxide by adding one oxygen atom to carbon-carbon double bond. As such an epoxidation method is known a method that the epoxidation is carried out in an inert organic solvent such as dichloromethane or the like by using an organic peracid as an epoxidizing agent.

There is recently known a method for synthesizing an optically active epoxide by catalytically oxidizing a prochiralic alkene with an asymmetric catalyst. This method using the asymmetric catalyst is a very important technique because it is possible to supply a great amount of an optically active compound from a tiny amount of the asymmetric catalyst.

Also, an epoxidation method using a cinnamate as a substrate of the catalyst.

However, an industrially mass-producible method is not known up to the present time. Furthermore, there are problems in the generality of the substrate. That is, only the cinnamate is known as the substrate of catalyst, so that there is a problem that the conventional catalyst used in the cinnamate can not be applied to a general substrate other than the cinnamate. Because, when the conventional catalyst is applied to a substrate containing a functional group such as carbon-carbon double bond, ketone or the like in its molecule, since such a catalyst is very high in the reactivity, a side reaction with such a functional group is caused and hence it is impossible to achieve an adequate epoxidation reaction.

Therefore, even if a compound containing a functional group such as carbon-carbon double bond, ketone or the like in its molecule is used as a substrate, it is desired to develop a method of producing an epoxide by using a catalyst capable of promoting the epoxidation reaction. If such a method is established, it is possible to simply synthesize an optically active compound useful for drug medicines in a large quantity. However, a convenient method for producing epoxide is no existence at this moment.

SUMMARY OF THE INVENTION

It is, therefore, an object of the invention to provide a general and multi-purpose method of producing an epoxide.

In order to achieve the above object, the inventors have made developments of asymmetric catalysts in the catalytic asymmetric epoxidation of unsaturated compounds and studies on the estimation of reactivity using calculation chemistry, and found out the following complexes and a method for producing an epoxide by using such a complex as a catalyst.

The complex according to the invention is characterized by representing the following general formula (I):

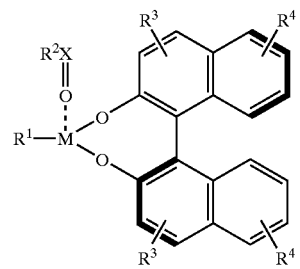

wherein X is P or As, and M is a rare earth metal, and $R^1$ is an alkoxy group or an alkyl peroxy group, and $R^2$ is a residue of a phenyl derivative, a residue of a heterocyclic compound or an alkyl group, and each of $R^3$ and $R^4$ is a substituent on an aromatic ring.

Also, the complex according to the invention is characterized by representing the following general formula (II):

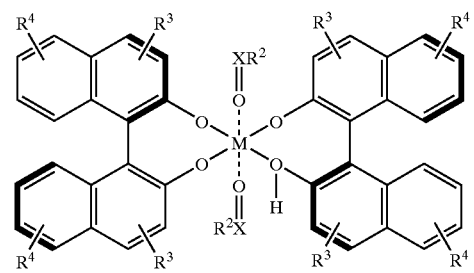

wherein X is P or As, and M is a rare earth metal, and $R^2$ is a residue of a phenyl derivative, a residue of a heterocyclic compound or an alkyl group, and each of $R^3$ and $R^4$ is a substituent on an aromatic ring.

Furthermore, the complex according to the invention is characterized by representing the following general formula (III):

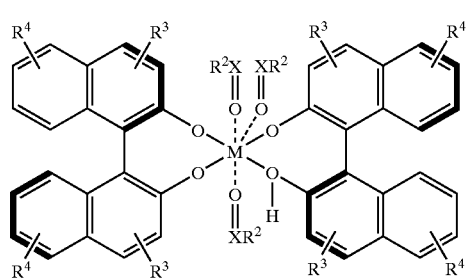

wherein X is P or As, and M is a rare earth metal, and $R^2$ is a residue of a phenyl derivative, a residue of a heterocyclic compound or an alkyl group, and each of $R^3$ and $R^4$ is a substituent on an aromatic ring.

In a preferable embodiment of the invention, M is at least one selected from the group consisting of La, Sm, Dy, Yb.

The asymmetric catalyst according to the invention is characterized by comprising the complex represented by the above general formula (I), (II) or (III).

The method for producing epoxide according to the invention is characterized by reacting an unsaturated amide or an unsaturated ketone with an oxidizing agent in the presence of the above asymmetric catalyst.

In a preferable embodiment of the method according to the invention, the unsaturated amide is an α,β-unsaturated active amide having a nitrogen-containing heterocycle such as an imidazole derivative, an oxazolidinon or the like.

In another preferable embodiment of the method according to the invention, the unsaturated ketone is at least one selected from the group consisting of trans-α,β-unsaturated ketones, cis-α,β-unsaturated ketones, α,β,γ,δ-unsaturated ketones.

In the other preferable embodiment of the method according to the invention, the oxidizing agent is at least one selected from the group consisting of t-butyl hydroperoxide (TBHP), cumene hydroperoxide (CMHP) and trityl hydroperoxide (TrOOH).

In a further preferable embodiment of the method according to the invention, the reaction is carried out in the presence of a coordinating solvent.

In a still further preferable embodiment of the method according to the invention, the coordinating solvent is selected from the group consisting of tetrahydrofuran (THF), dimethoxyethane and ether.

In a yet further preferable embodiment of the method according to the invention, the reaction is further carried out with an alcohol, a metallic amide, a reducing agent, a metallic enolate or the like to obtain an α,β-epoxy ester, an α,β-epoxy amide, an α,β-epoxy aldehyde and γ,δ-epoxy-β-ketoester.

DETAILED DESCRIPTION OF THE INVENTION

The complex according to the invention is represented by the general formula (I):

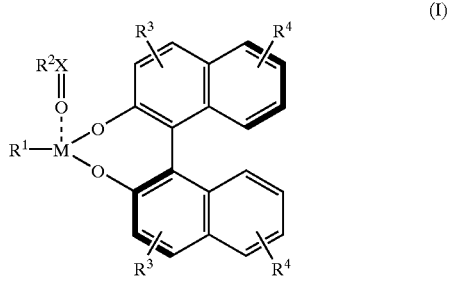

(I)

wherein X is P or As, and M is a rare earth metal, and $R^1$ is an alkoxy group or an alkyl peroxy group, and $R^2$ is a residue of a phenyl derivative, a residue of a heterocyclic compound or an alkyl group, and each of $R^3$ and $R^4$ is a substituent on an aromatic ring.

Also, the complex according to the invention is represented by the general formula (II):

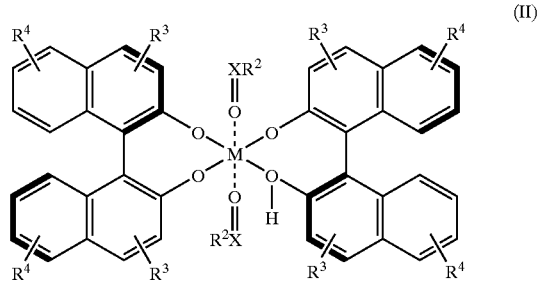

(II)

wherein X is P or As, and M is a rare earth metal, and $R^2$ is a residue of a phenyl derivative, a residue of a heterocyclic compound or an alkyl group, and each of $R^3$ and $R^4$ is a substituent on an aromatic ring.

Furthermore, the complex according to the invention is represented by the general formula (III):

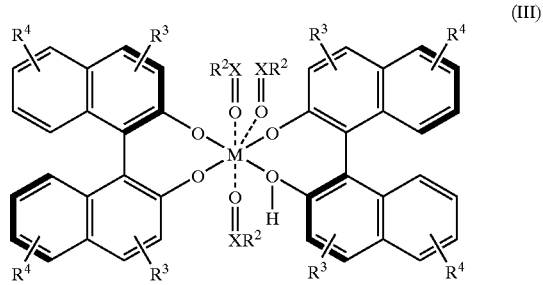

(III)

wherein X is P or As, and M is a rare earth metal, and $R^2$ is a residue of a phenyl derivative, a residue of a heterocyclic compound or an alkyl group, and each of $R^3$ and $R^4$ is a substituent on an aromatic ring.

The inventors have focused attention on substrates other than cinnamate in view of the generality of the substrate. However, the conventionally used catalyst is very low in the functional group selectivity, so that it can not be applied to a substrate containing a functional group such as carbon-carbon double bond, ketone or the like.

Therefore, the inventors have attempted to develop various sorts of the catalyst for the epoxidation of unsaturated compounds and found out that the aforementioned complexes are effective as the catalyst.

In the above formulae (I)–(III), M is a rare earth metal. The rare earth metal is not particularly limited. As the rare earth metal, mention may be made of La, Ce, Pr, Nd, Pm, Sm, Eu, Gd, Dy, Ho, Er and Yb. From a viewpoint of a higher enantioselectivity, at least one selected from the group consisting of La, Sm, Dy, Yb is preferable as the rare earth metal.

Also, each of $R^3$ and $R^4$ is a substituent on an aromatic ring and is not particularly limited. As the substituent, mention may be made of an alkyl group, an ether, a halogen atom, an amido group, an ester and so on.

The complex having a bone structure of the above formula (I), (II) or (III) can be synthesized as follows.

That is, the complex can be obtained by reacting a metal isopropoxide, an optically active binaphthol and triphenyl oxide in a solvent such as THF or the like at room temperature for from 30 minutes to 1 hour.

In case of the complex (1:1:1) shown in the formula (I), a ratio of metal isopropoxide to optically active binaphthol (BINOL derivative) to triphenyl oxide is about 1:about 1:about 1. In view of a higher reactivity, the ratio is preferable to be metal isopropoxide:BINOL derivative:triphenyl oxide=about 100 mol %:about 100 mol %:about 100 mol %.

In case of the complex (1:2:2) shown in the formula (II), a ratio of metal isopropoxide to optically active BINOL derivative to triphenyl oxide is about 1:about 2:about 2. In view of the stability of the complex in the solution, the ratio is preferable to be metal isopropoxide:BINOL derivative:triphenyl oxide=about 100 mol %:about 200 mol %:about 200 mol %.

In case of the complex (1:2:3) shown in the formula (III), a ratio of metal isopropoxide to optically active BINOL derivative to triphenyl oxide is about 1:about 2:about 3. From a viewpoint that the crystallization of the complex is made easy, the ratio is preferable to be metal isopropoxide:BINOL derivative:triphenyl oxide=about 100 mol %:about 100 mol %:about 300 mol %.

Especially, the excessive amount of the metal isopropoxide promotes the epoxidation reaction as mentioned later. Therefore, if it is intended to promote the epoxidation reaction, the ratio of the metal isopropoxide is made high. For example, it is desirable to increase the ratio of the metal isopropoxide up to 1 equivalent with respect to a chiral ligand in order to promote the reaction.

The thus obtained complex acts as an asymmetric catalyst. The asymmetric catalyst according to the invention comprises the complex represented by the above formula (I), (II) or (III). The above conditions of the metal mentioned on the complex can be applied for the catalyst. The asymmetric catalyst means a catalyst itself having an ability of producing an optically active substance, rightly an enantio-separating catalyst. The asymmetric catalyst according to the invention can epoxidize an unsaturated amide or an unsaturated ketone high-enantioselectively as mentioned later.

Next, the method for producing an epoxide according to the invention will be explained. According to the invention, the epoxide can be obtained by reacting the unsaturated amide or unsaturated ketone with an oxidizing agent in the presence of the asymmetric catalyst. The term "unsaturated" used herein means a so-called carbon-carbon double bond.

In the epoxidation reaction of the unsaturated amide, epoxy peroxy ester is a stable intermediate produced in the reaction system and can be reacted with an alcohol, a metal amide, a reducing agent, an enolate or the like to easily provide $\alpha,\beta$-epoxy ester, $\alpha,\beta$-epoxy amide, $\alpha,\beta$-epoxy aldehyde, $\gamma,\delta$-epoxy $\beta$-keto ester, so that it is an intermediate having a very high versatility. In this case, methanol or the like may be mentioned as the alcohol.

The unsaturated amide or unsaturated ketone intended for the asymmetric catalyst according to the invention is not particularly limited. As the unsaturated ketone, mention may be made of any unsaturated ketones including unsaturated aliphatic ketones, unsaturated aromatic ketones and the like. For example, the unsaturated ketone may include at least one selected from the group consisting of trans-$\alpha,\beta$-unsaturated ketones, cis-$\alpha,\beta$-unsaturated ketones and $\alpha,\beta,\gamma,\delta$-unsaturated ketones.

As the unsaturated amide, mention may be made of unsaturated active amides having a nitrogen-containing heterocycle such as imidazole derivatives, oxazolidinone and the like.

As the oxidizing agent may be mentioned a peroxide. The peroxide may include t-butyl hydroperoxide (TBHP), cumene hydroperoxide (CMHP), trityl hydroperoxide (TrOOH) and so on. Among them, TBHP is preferable as the oxidizing agent from a viewpoint of a high reactivity.

A solvent used in the epoxidation reaction is not particularly limited. As the solvent, mention may be made of a low-polarity solvent such as toluene, $CH_2Cl_2$ or thelike, and a coordination solvent such as tetrahydrofuran (THF), dimethoxyethane, ether or the like. In view of the rise of the reaction rate, tetrahydrofuran (THF) is preferable as the solvent.

The reaction temperature for the epoxidation reaction is not particularly limited, but is 0–40° C., preferably 15–25° C. from a viewpoint of a high enantioselectivity. The lower limit of 0° C. is for maintaining the reactivity of the epoxidation reaction, and the upper limit of 40° C. is for stabilizing the complex and TBHP.

Furthermore, the concentration of the amide or ketone is not particularly limited and may be properly changed in accordance with the interest product. The reaction rate tends to become high as the concentration of the amide or ketone is high. However, the reaction rate does not increase even if the concentration of the substrate or the concentration of the amide or ketone is so increased after the arrival to a maximum reaction rate because the concentration of the substance is saturated in the vicinity of the maximum reaction rate.

Moreover, various additives may be added to the reaction solution. For example, a drying agent such as MS4A or the like may be added.

MS is one of crystalline zeolites and there are 3A, 4A, 5A and so on in accordance with the pore size in the crystal. For example, 4A means that the pore size is about 4 angstroms. A main function of MS is for incorporating water in the reaction solution into the pores to remove a slight amount of water.

BRIEF DESCRIPTION OF THE DRAWINGS

The invention will be described with reference to the accompanying drawings, wherein.

The following examples are given in illustration of the invention and are not intended as limitations thereof. Moreover, it is naturally possible to properly change the invention without departing from the spirit thereof.

EXAMPLE 1

A complex according to the invention is synthesized as follows. At first, lanthanum isopropoxide is used as a metal isopropoxide and triphenyl arsinoxide is used as triphenyl oxide. Lanthanum isopropoxide, optically active binaphtol (BINOL derivative) and triphenyl arsinoxide are mixed at a ratio of 1:1:1 mol % in an argon atmosphere at room temperature for 30 minutes to 1 hour to obtain La-BINOL derivative-$Ph_3As=O$ complex.

The thus obtained complex has the following properties.

$^1$H NMR(500 MHz, $D_2O$): 7.63, 7.45, 7.44, 7.42, 7.37, 7.18, 7.10, 6.97, 6.91, 4.68, 3.99, 3.97, 3.96, 3.95, 3.94, 3.91, 3.90, 3.89, 3.77, 3.76, 3.75, 3.63, 3.61, 3.60, 2.07, 2.06, 2.04, 2.03, 2.02, 1.94, 1.91, 1.81, 1.79, 1.78, 1.77, 1.75, 1.22, 1.21, 0.26

$^{13}$C NMR (125 MHz, $D_2O$): 131.96, 128.78, 128.30, 127.90, 126.77, 126.59, 67.71, 67.64, 67.52, 67.38, 67.06, 62.96, 26.07, 25.89, 25.86, 25.78, 25.57, 25.53, 25.23

IR: 3468, 3051, 2973, 2857, 1614, 1588, 1498, 1461, 1438, 1422, 1343, 1265, 1245, 1069, 993, 956, 902, 820, 741, 692 $cm^{-1}$

Figure 1A:
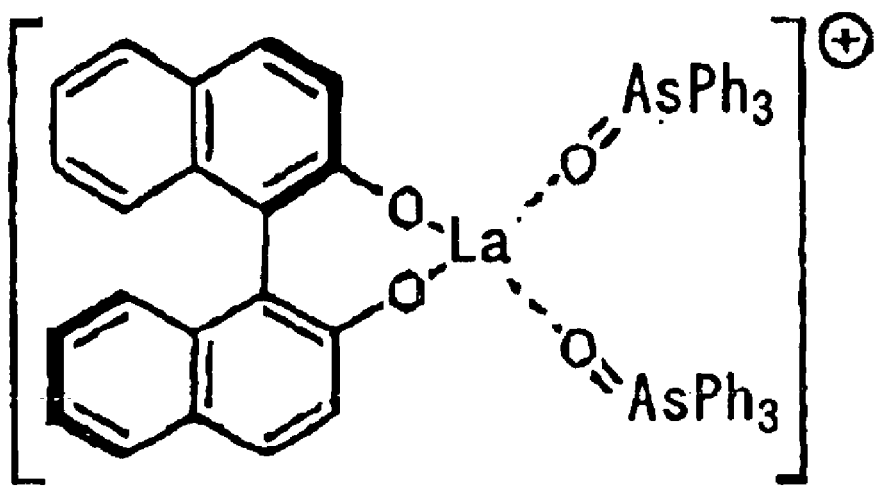
FIGS. 1a and 1b are views showing an embodiment of the complex according to the invention.
Figure 1B:
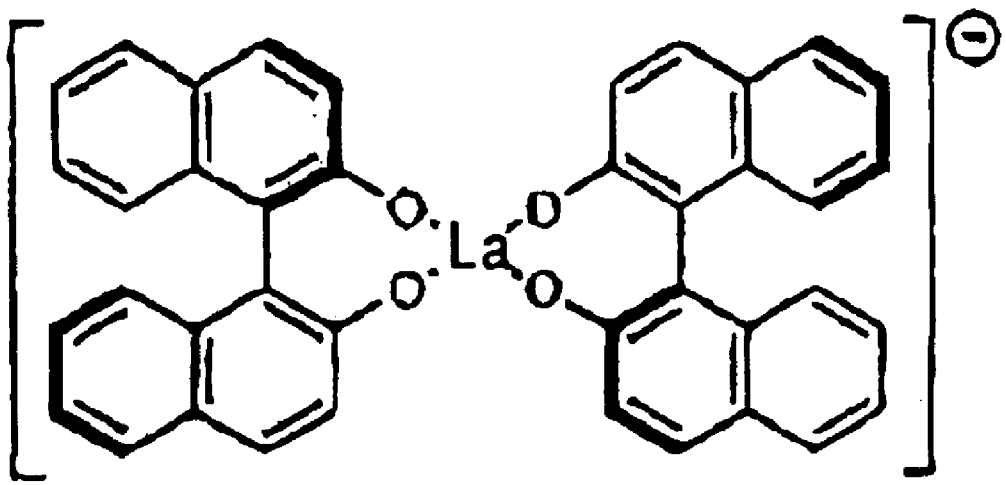
Figure 2A:
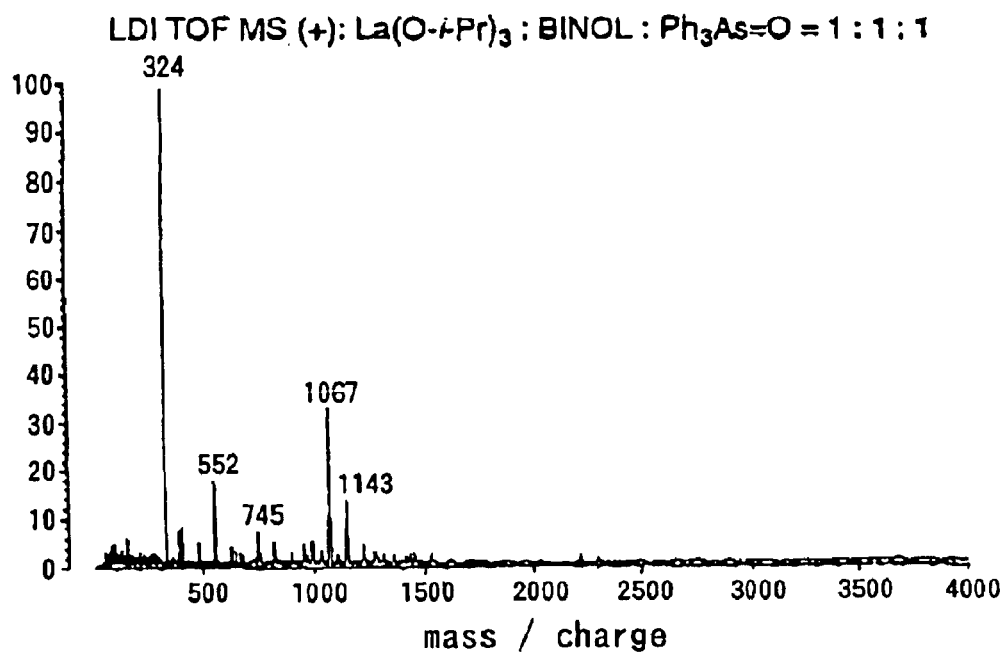
FIGS. 2a and 2b are graphs showing mass spectrometry results of an of embodiment of the complex according to the invention.
Figure 2B:
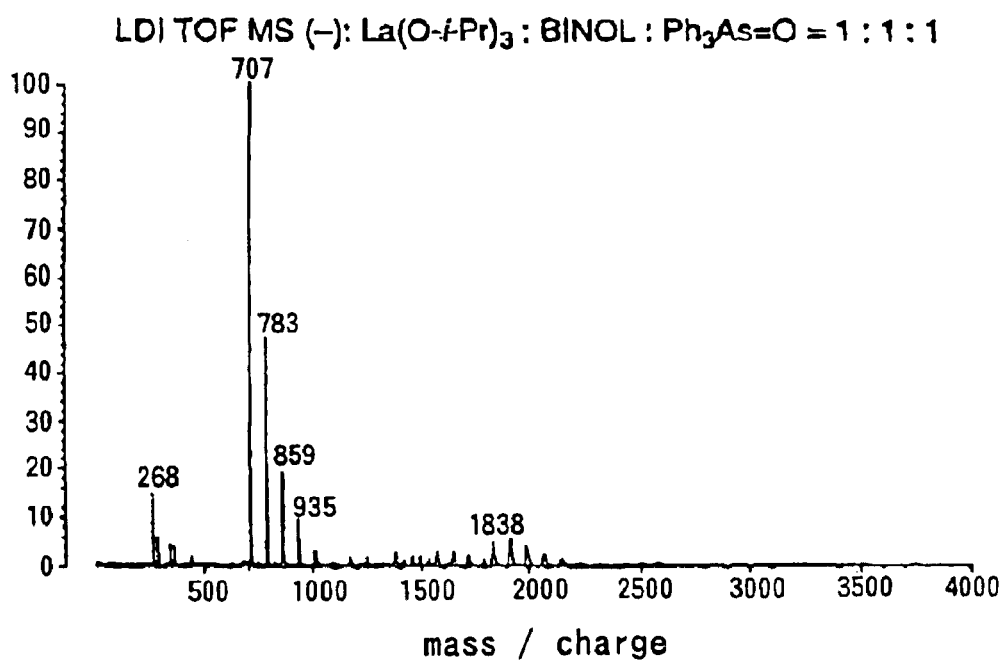
Figure 4A:
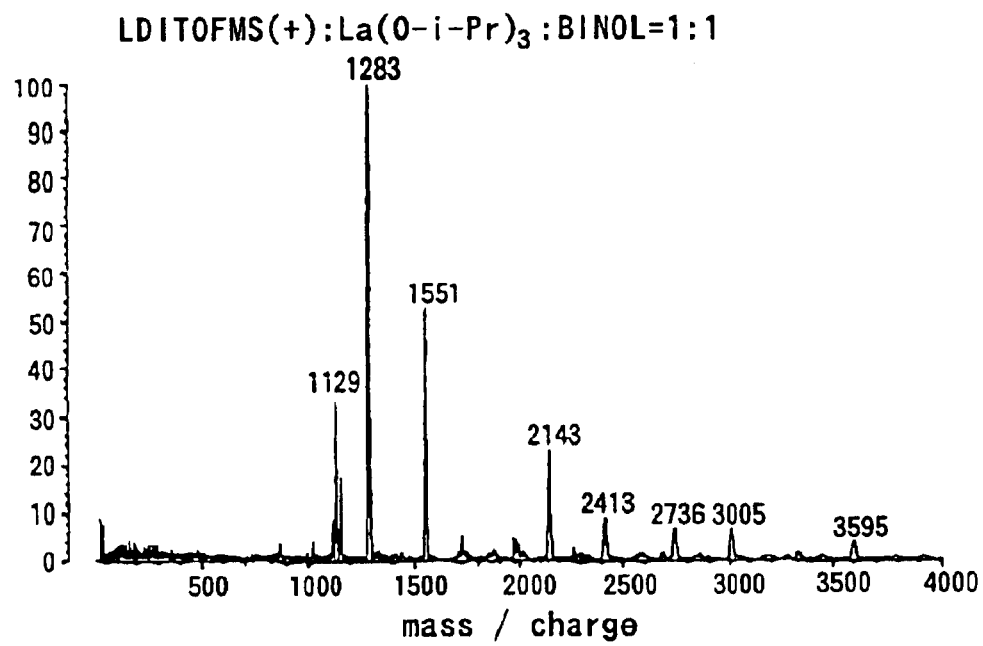
FIGS. 4a and 4b are graphs showing results of La-BINOL complex in the absence of $Ph_3As=O$ according to LDI TOF MS.
Figure 4B:
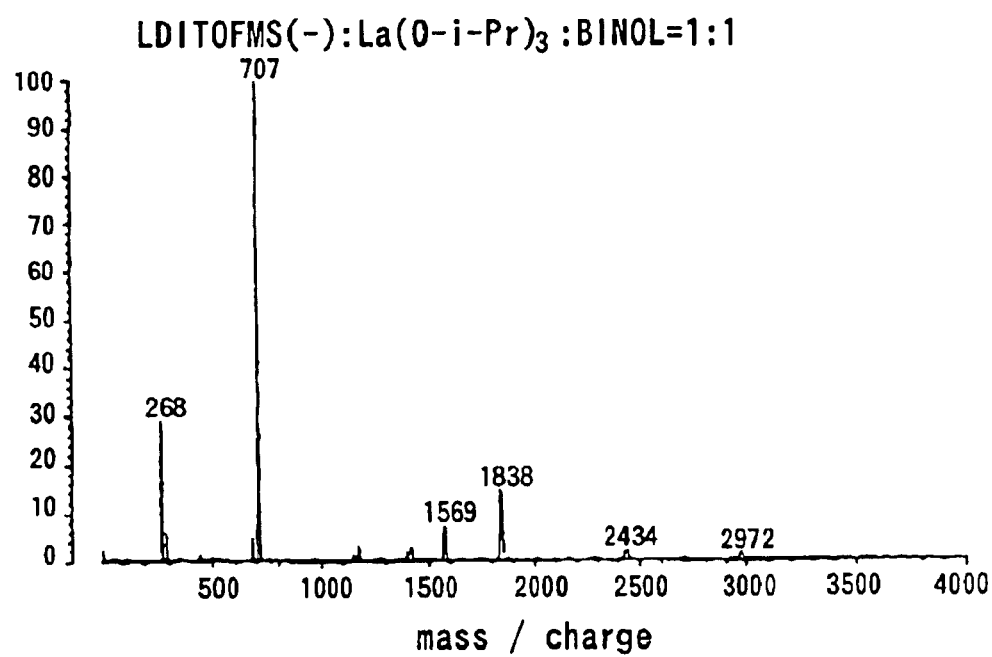

Although $^1$H NMR(500 MHz, $D_2O$) and $^{13}$C NMR(125 MHz, $D_2O$) in THF solution of the La-BINOL-$Ph_3As=O$ complex synthesized according to the above method are measured, any spectra only indicate a broadened peak at an aromatic region. These results only suggest that the La-BINOL-Ph$_3$As=O complex is existent at an oligomerically associated state even in the presence of Ph$_3$As=O, or various complexes may exist at a very fast equilibrium state in the complex solution. However, as a result of mass spectrometry according to LDI TOF MS, remarkable peaks are observed at 1067 in a positive mode and at 707 in a negative mode (FIG. 2). FIG. 2 shows the result of mass spectrometry according to LDI TOF MS for the complex. This mass spectrometry shows that the complex has a structure (a) and (b) shown in FIG. 1, respectively. From these results, it is considered that the complex mainly existing in the solution is actually La:BINOL derivative:As= 1:2:2 as shown in the formula (II). On the other hand, in case of La-BINOL complex containing no Ph$_3$As=O, peaks showing an oligomer complex with a molecular weight of several thousands are observed according to LDI TOF MS (FIG. 4).

As seen from the above results, it is considered that the La-BINOL derivative complex has a very complicated oligomeric structure, but it is easy to take a monomeric structure by adding Ph$_3$As=O because an oxygen in Ph$_3$As=O coordinates to La, which is considered to promote the epoxidation when the complex according to the invention is used as a catalyst. This is also supported from a fact that only a part of La used in case of the oligomeric structure actually serves as a catalyst.

Figure 3A:
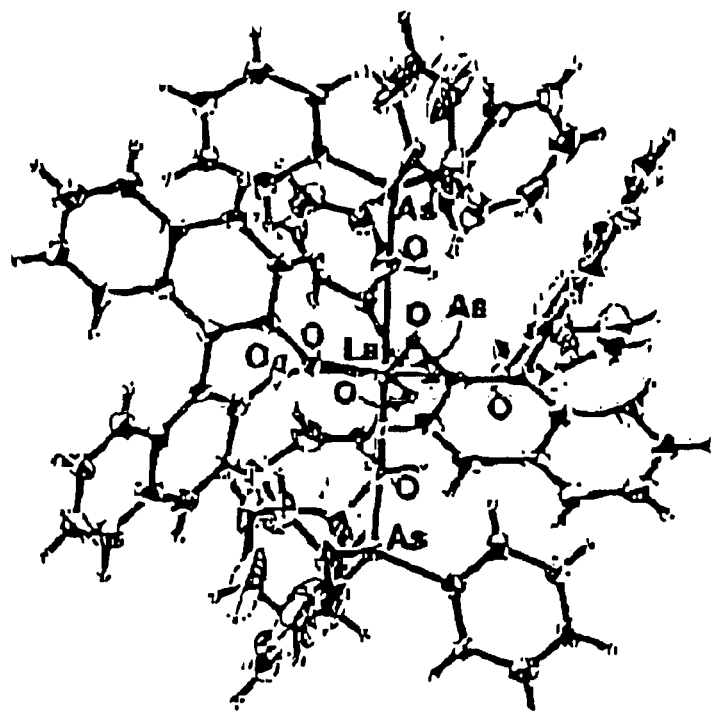
FIGS. 3a and 3b are views showing a crystal structure of an embodiment of the complex according to the invention.
Figure 3B:
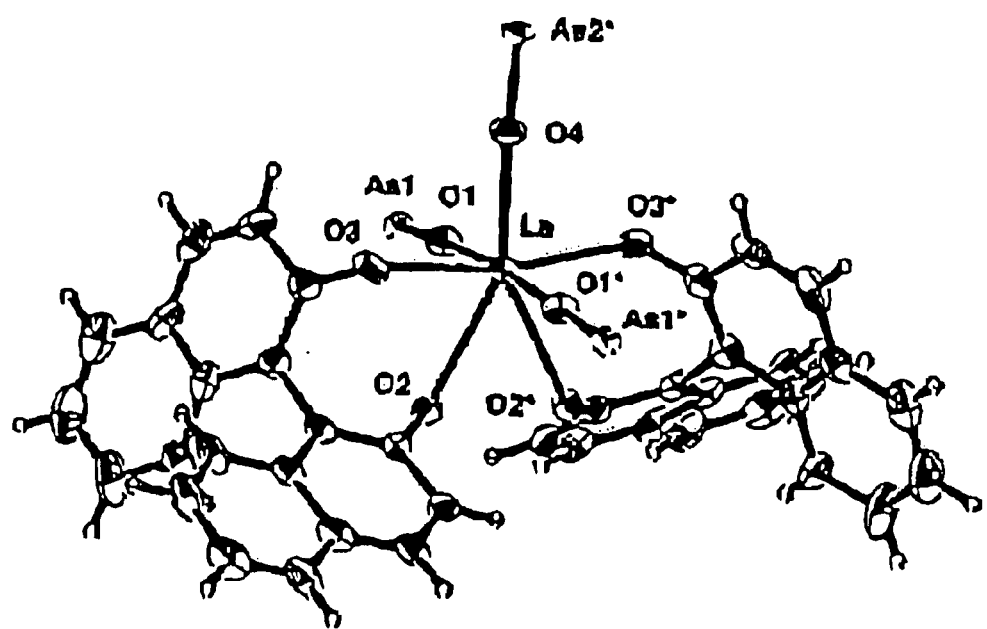

It is supported from an X-ray crystal structure analysis that the La-BINOL derivative-Ph$_3$As=O complex is a monomer. When Ph$_3$As=O is further added to a catalyst system made of La(O-i-Pr)$_3$-BINOL derivative-Ph$_3$As=O of 1:1:1, the crystal is precipitated to have a structure comprising La:BINOL derivative:As=1:2:3 as shown in FIG. 3.

Although the crystal of La:BINOL derivative:As=1:2:3 itself is not so high in the catalytic activity, if a metal isopropoxide such as La(O-iPr)$_3$ or the like is added to the complex of La:BINOL derivative:As=1:2:3 so as to put close to an ideal ratio, the catalytic activity and astmmetric yield are recovered, so that it is considered that a true catalyst species is close to the structure through the above X-ray analysis.

EXAMPLE 2

Next, the ratio of three components of metal isopropoxide, BINOL derivative and triphenyloxide is examined.

Lanthanum isopropoxide and triphenyl arsineoxide are used as metal isopropoxide and triphenyloxide, respectively.

When epoxide is synthesized by the epoxidation reaction using the crystal as the catalyst under conditions that the reaction temperature is room temperature and the reaction time is 3 hours, the yield is 71% and enantiomer excess is 67% ee.

Also, when epoxide is synthesized by the epoxidation reaction using a solution of the complex of La-BINOL derivative-As prepared in a ratio by mol % of 1:2:2, which is considered to mainly exist in the solution, under conditions that the reaction temperature is room temperature and the reaction time is 1.2 hours, the yield is 93% and enantiomer excess is 92% ee.

Furthermore, the examination is conducted by changing the ratio of three components from 1:2:2 to 1:1:1. In this case, the reaction temperature is 25° C. and the reaction time is 15 minutes. THF is used as a solvent. Moreover, MS4A (molecular sieve 4A) is added to the reaction solution. The results are shown in Table 1.

TABLE 1

| entry | La(O—i-Pr)$_3$ (x mol %) | (R)-BINOL (y mol %) | Ph$_3$AsmO (z mol %) | ratio (x:y:z) | yield (%) | ee (%) |
|---|---|---|---|---|---|---|
| 1 | 5 | 10 | 10 | 1:2:2 | 57 | 95 |
| 2 | 5 | 8.3 | 8.3 | 1.2:2:2 | 71 | 96 |
| 3 | 5 | 7.1 | 7.1 | 1.4:2:2 | 79 | 94 |
| 4 | 5 | 6.3 | 6.3 | 1.6:2:2 | 82 | 95 |
| 5 | 5 | 5.6 | 5.6 | 1.8:2:2 | 88 | 94 |
| 6 | 5 | 5 | 5 | 2:2:2 | 98 | 96 |

As seen from Table 1, when the ratio is changed from 1:2:2 to 1:1:1, the asymmetric yield is not changed, but the chemical yield is gradually raised and the best result is obtained in case of the preparation in the ratio of 1:1:1.

As a result, it is anticipated that the metal isopropoxide existing in 1 equivalent with respect to the complex of the formula (II) that may be mainly existent in the reaction solution plays an important role in the promotion of the reaction.

Now, when an initial rate of the reaction is measured by adding La(O-i-Pr)$_3$ to the solution of the complex of La-BINOL derivative-Ph$_3$As=O prepared in a ratio of 1:2:2, the great rise of the initial rate is observed, from which it is understood that La(O-i-Pr)$_3$ excessively existing for the complex of the formula (II) has a great effect for the promotion of the reaction.

From the above is considered a reaction mechanism shown by the following reaction formula:

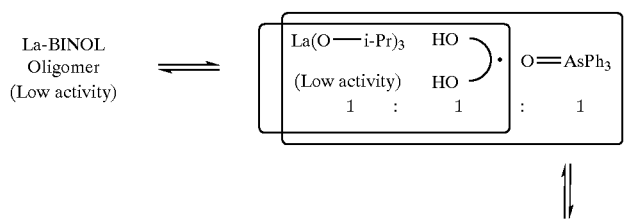

-continued

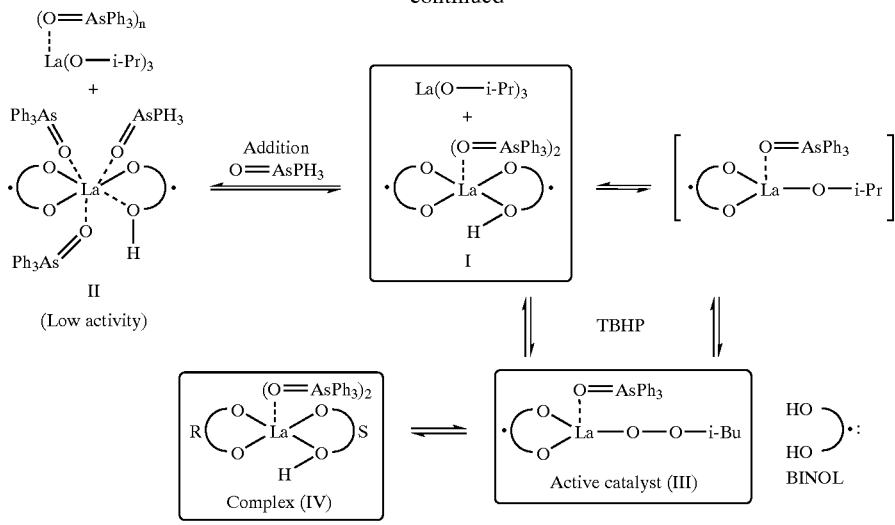

It is considered that the stable complex of the formula (II) mainly produced in the solution of the complex of La(O-i-Pr)$_3$-BINOL derivative-Ph$_3$As=O prepared in a ratio of 1:1:1 forms an active complex of La-BINOL derivative-Ph$_3$As=O of 1:1:1 shown by the formula (I) through the reaction of La(O-i-Pr)$_3$ existing in the reaction system with TBHP, which serves as a catalyst for the epoxidation reaction.

That is, it is suggested that the excessive La(O-i-Pr)$_3$ is important for the activation of the reaction. Also, it is confirmed that although the various complexes of the formulae (I)–(III) have a function as the catalyst for the epoxidation, the reaction become late unless the metal isopropoxide such as La(O-i-Pr)$_3$ is added.

EXAMPLE 3

The epoxidation is examined by using various catalysts in which chalcone among enones is used as a substrate.

Concretely, the enantiomer selectivity is examined when chalcone is reacted with TBHP by using various catalysts.

The reaction formula is as follows.

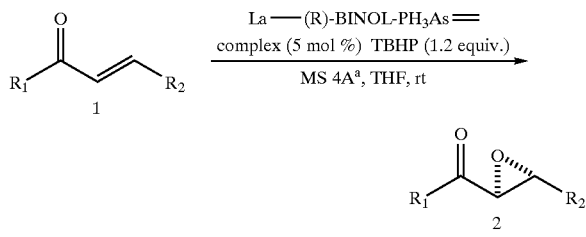

The results on the enantiomer selectivity of chalcone using various catalysts are shown in Table 2.

TABLE 2

| entry | catalyst (mol %) | additives (mol %) | time (min) | yield (%) | ee (%) |
|---|---|---|---|---|---|
| 1 | La—(R)-BINOL (1:1) (10) | — | 90 | 92 | 71 |
| 2 | La—(R)-BINOL (1:1) (10) | Ph$_3$P=O (10) | 30 | 98 | 97 |

TABLE 2-continued

| entry | catalyst (mol %) | additives (mol %) | time (min) | yield (%) | ee (%) |
|---|---|---|---|---|---|
| 3 | La—(R)-BINOL (1:1) (10) | Ph$_3$P=O (30) | 30 | 97 | 97 |
| 4 | La—(R)-BINOL (1:1) (10) | Ph$_3$P=O (20) | 30 | 94 | 95 |
| 5 | La—(R)-BINOL (1:1) (10) | Ph$_3$P=O (10) | 30 | 93 | 94 |
| 6 | La—(R)-BINOL (1:1) (10) | Ph$_3$As=O (40) | 60 | 92 | 95 |
| 7 | La—(R)-BINOL (1:1) (10) | Ph$_3$As=O (30) | 30 | 92 | 93 |
| 8 | La—(R)-BINOL (1:1) (10) | Ph$_3$As=O (20) | 30 | 96 | 95 |
| 9 | La—(R)-BINOL (1:1) (10) | Ph$_3$As=O (10) | 3 | 95 | 97 |
| 10 | La—(O—i-Pr)$_3$ (10) | — | 480 | 90 | — |
| 11 | La—(O—i-Pr)$_3$ (10) | Ph$_3$As=O (10) | 480 | 64 | — |

In Table 2, ee is an enantiomer excess. As a result, the lowering of the chemical yield and asymmetric yield is observed as the amount of Ph$_3$P=O added is decreased in the epoxidation of chalcone (Table 2, entry 2–5).

On the other hand, in the case of using Ph$_3$As=O, the improvement of the chemical yield and asymmetric yield is revealed as the addition amount is decreased (Table 2, entry 6–9). Also, it is confirmed that the reaction is promoted by a chiral ligand because the reaction is very slow under the conditions using La(O-i-Pr)$_3$ and La(O-i-Pr)$_3$-BINOL derivative-Ph$_3$As=O as a catalyst (Table 2, entry 10, 11).

EXAMPLE 4

In this example, an optimum condition of La(O-i-Pr)$_3$-BINOL derivative-Ph$_3$As=O=1:1:1 obtained in the epoxidation reaction of chalcone is ed to various enones. The results are shown in Table 3.

TABLE 3

| entry | enones | $R_1$ | $R_2$ | epoxy ketone | time (h) | yield (%) | ee (%) |
|---|---|---|---|---|---|---|---|
| 1 | 1a | Ph | Ph | 2a | 0.25 (7)[b] | 99 (93)[b] | 96 (91)[b] |
| 2[a] | 1a | Ph | Ph | 2a | 3 | 97 | 89 |
| 3 | 1b | o-MOMO-$C_8H_4$ | Ph | 2b | 4 | 91 | 95 |
| 4 | 1c | Ph | i-Pr | 2c | 1.5 | 95 | 94 |
| 5 | 1d | $CH_3$ | Ph | 2d | 6 (96)[b] | 92 (83)[b] | >99 (94)[b] |
| 6 | 1e | $CH_3$ | $CH_2CH_2Ph$ | 2e | 1.5 | 98 | 92 |
| 7 | 1f | $CH_3$ | $C_5H_{11}$ | 2f | 1.5 | 89 | 95 |
| 8 | 1g | i-Pr | Ph | 2g | 8 | 72 | 95 |
| 9 | 1h | t-Bu | Ph | 2h | 7 | 94 | 98 |
| 10 | 1i | Ph | $CH=CHC_3H_7$ | 2i | 3 | 95 | 96 |

In Table 3, a superscript "a" means a case using a 1 mol % catalyst, and a superscript "b" means a case using a 5 mol % Ln-BINOL complex. An excellent result is obtained in not only an aryl ketone type of the enone (Table 3, entry 1–4) but also an alkyl keton type of the enone (Table 3, entry 5–9) by using the 1–5 mol % catalysts. In general, it is known that it is difficult to conduct the catalytic asymmetric epoxidation reaction of the alkyl ketone type enone capable of the enolisation, so that the reaction according to the incvention can be said to be a high generality reaction. Furthermore, the significant improvement of the reactivity is found as compared with the condition of the catalytic asymmetric epoxidation reaction using the conventional Ln-BINOL complex. Further, α,β-epoxy ketone is obtained in a perfect site selectivity even when dienone such as 1i is used as a substrate (Table 3, entry 10).

Moreover, in order to examine an influence of a central metal, the reaction using Yb as a heavy rare earth atom is carried out in the same manner as in Example 3 to obtain a result shown in Table 3.

EXAMPLE 5

The epoxidation reaction is carried out by using various active unsaturated amides as a substrate. A possibility of using the active unsaturated amide as a substrate is derived from the estimations that the conversion of alcohol for imidazole reduces a minimum unoccupied orbital energy based on the molecular orbital calculations at initial stage and thereafter weak nucleophilic atom attacks β-carbon rather than carbonyl carbon.

The epoxidation is carried out in the presence of a catalyst (20 mol %) prepared in a ratio of La(O-i-Pr)$_3$-BINOL derivative-$Ph_3As=O$ of 1:1:1 as described in Example 1 using various active unsaturated amides as a substrate. The reaction formula is shown as follows.

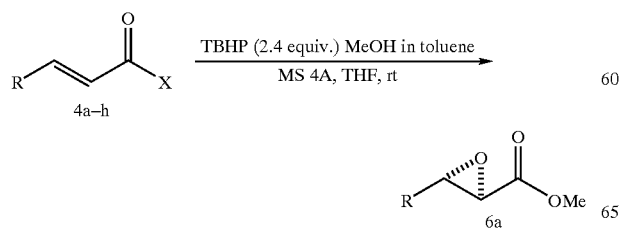

The results are shown in Table 4.

TABLE 4

| entry | substrates | | time (h) | yield (%)[a] | ee (%)[b] |
|---|---|---|---|---|---|
| 1 | (N-methylimidazole enone) | 4a | 4 | 86 | 91 |
| 2 | (2-methyl N-methylimidazole enone) | 4b | 12 | 70 | 77 |
| 3 | (2-phenyl N-methylimidazole enone) | 4c | 12 | 69 | 87 |
| 4 | (5-methyl N-methylimidazole enone) | 4d | 3 | 85 | 92 |
| 5 | (5-phenyl N-methylimidazole enone) | 4e | 1 | 91 | 94 |
| 6 | (N-methylbenzimidazole enone) | 4f | 24 | 80 | 63 |
| 7 | (N-methyltriazole enone) | 4g | 1 | trace | — |
| 8 | (N-methyloxazolidinone enone) | 4h | 24 | 73 | 87 |

In Table 4, a superscript "a" means an isolated yield and a superscript "b" means that the value is determined by HPLC analysis. As shown in Table 4, 4-phenyl imidazoride 4e having a LUMO lower than that of imidazoride 4a gives a best result in the reactivity, chemical yield and enantiomer excess (1 hour, yield 91% ee). As seen from these results, 4-phenyl imidazoride efficiently enhances the reaction through β-carbon toward the weak nucleophilic atom.

EXAMPLE 6

The epoxidation reaction regarding different substrates is examined in the same manner as in Example 5. The results are shown in Table 5.

TABLE 5

| entry | R | substrates | products | time (h) | yield (%)[a] | ee (%)[b] |
|---|---|---|---|---|---|---|
| 1 | Ph- | 4e | 6a | 3.5 | 86 | 92 |
| 2[c] | Ph- | 4e | 6a | 12 | 73 | 85 |
| 3 | 4-Cl—C$_6$H$_4$— | 4i | 6i | 5 | 91 | 93 |
| 4[d] | 4-Br—C$_6$H$_4$— | 4j | 6j | 4 | 86 | 89 |
| 5 | 4-MeO—C$_6$H$_4$— | 4k | 6k | 6 | 80 | 91 |
| 6 | Ph⁀⁀ | 4l | 61 | 1 | 86 | 83 |
| 7 | ⁀⁀⁀ | 4m | 6m | 2 | 93[e] | 86[f] |
| 8 | ⁀⁀⁀ | 4n | 6n | 1.5 | 92[e] | 79[f] |
| 9 | Ph⁀⁀ | 4o | 6o | 2 | 85 | 82 |
| 10 | O⁀⁀ | 4p | 6p | 4 | 81[e] | 81[f] |
| 11 | Cy⁀ | 4q | 6q | 4 | 72[e] | 88[f] |

In Table 5, a superscript "a" means an isolated yield, a superscript "b" means that the value is determined by HPLC analysis, a superscript "c" shows the use of a 5 mol % catalyst, a superscript "d" means that 4-methyl imidazoride is used for the low solubility of the corresponding 4-phenyl imidazoride, a superscript "e" means a yield of tert-butyl peroxy carboxylic acid ester in which the addition of methanol to the reaction produces the corresponding methyl ester at the same yield, and a superscript "f" means enatiomer excess determined after the change to the corresponding 4-methoxy benzyl ester.

As a result, corresponding epoxides 6a, i–q are obtained, which have a generality for the epoxidation of various α,β-unsaturated carboxylic acid 4-phenyl imidazorides. When the 10 mol % La-BINOL-Ph$_3$A=O catalyst is used at room temperature, all reactions are progressed and terminated within a reasonable time. In case of 4e, the reaction is promoted even in the use of the 5 mol % La-BINOL-Ph$_3$As=O catalyst to efficiently obtain 6a (yield 73%, 85% ee). The other cinnamic acid derivatives having an electron acceptor (Table 5, entry 3, 4) or an electron donor (Table 5, entry 5) on an aromatic ring are smoothly epoxidized to obtain 6i,j or 6k at a good enatiomer excess (89–93% ee). Epoxide 6k is a key intermediate as one of the most predominant calcium antagonists. This asymmetric catalyst system is effective for β-alkyl substituted α,β-unsaturated carboxylic acid type substrate having a reactivity higher than that of cinnamic acid type substrate (Table 5, entry 6–11). In both the first (Table 5, entry 11) and the second (Table 5, entry 11) alkyl substituted substrates, products are obtained in a high yield (72–93%) at a good enantiomer excess (79–88% ee). It is particularly noted that the reaction can be applied to functional groups such as carbon-carbon double bond (Table 5, entry 7–9) and ketone (Table 5, entry 10) without other excess oxidation.

EXAMPLE 7

In this example is examined the utility of peroxyester which is an isolated intermediate obtained by the epoxidation of the unsaturated amide. The isolated peroxyester is converted into α,β-epoxy ester 6a (89%), α,β-epoxy amide 9 (92%), α,β-epoxy aldehyde 10 (70%) and γ,δ-epoxy-β-ketoester 11 (77%) by adding lithium metaoxide, lithium amide, Red-Al (registered trademark), and lithium ester enolate without any epoxy ring opening reaction, respectively. The reaction formula is shown as follows. In the formula, methanol, THF, toluene are solvents. The reaction temperature is −78° C.

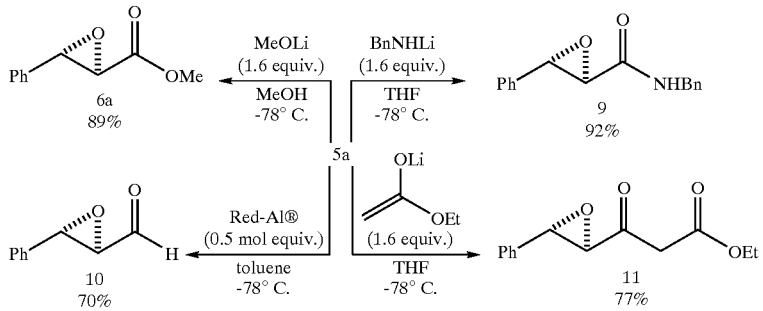

EXAMPLE 8

In this example is examined the effect of a rare earth metal when using various rare earth metals in the same manner as in Example 5. Concretely, 20 mol % Ln-BINOL-Ph$_3$As=O (1:1:1) is used. The results are shown in Table 6.

TABLE 6

| metal | reaction time | yield | ee |
|---|---|---|---|
| La | 1 h | 91% | 94% ee |
| Sm | 3 h | 89% | 80% ee |
| Dy | 5 h | 85% | 80% ee |
| Yb | 2 h | 87% | 94% ee |

As a result, each of the rare earth metals shows a high yield and a high enantiomer excess.

EXAMPLE 9

The effect of an additive is examined in the same manner as in Example 5. Concretely, 20 mol % La-BINOL (1:1) is used. Also, the equivalent of $Ph_3P=O$ is 4 for La, that is, La:BINOL:$Ph_3P=O$ is 1:1:4. The results are shown in Table 7.

TABLE 7

| additives | reaction time | yield | ee |
|---|---|---|---|
| none | 5 h | 65% | 85% ee |
| $Ph_3P=O$ | 5 h | 71% | more than 90% ee |

EXAMPLE 10

The effect of a chiral ligand is examined in the same manner as in Example 5. Concretely, 20 mol % La-chiral ligand-$Ph_3As=O$ (1:1:1) is used. The results are shown in Table 8.

TABLE 8

| ligand | reaction time | yield | ee |
|---|---|---|---|
| 6.6'-Br-BINOL | 5 h | 77% | 87% ee |

As seen from the above, good yield and enantiomor excess are shown even in BINOL derivatives such as 6,6'-Br-BINOL and the like.

EXAMPLE 11

The effect of an oxidant is examined in the same manner as in Example 5. Concretely, 20 mol % La-BINOL-$Ph_3As=O$ (1:1:1) is used. Specifically, the effect of the oxidant is examined with respect to TrOOH (TrOOH means that three methyl groups in TBHP are substituted with phenyl groups by $Ph_3COOH$) in stead of TBHP. The result is shown in Table 9.

TABLE 9

| reaction time | yield | ee |
|---|---|---|
| 24 h | trace | |

As a result, a slight amount of epoxide can be obtained.

The invention has an advantageous effect that the complex can be effectively used as an asymmetric catalyst.

Furthermore, the asymmetric catalyst according to the invention can attain a high-enantioselectively epoxidation of unsaturated amide or unsaturated ketone. Moreover, the invention has an advantageous effect that α,β-epoxy carboxylic acid derivatives as an intermediate can be easily converted into α,β-epoxy amide, α,β-epoxy aldehyde, γ,δ-epoxy-β-ketoester by various reactions.

What is claimed is:

1. A method for producing an epoxide characterized by reacting an unsaturated amide with an oxidizing agent in the presence of an asymmetric catalyst wherein the asymmetric catalyst comprises a complex selected from the group consisting of complexes represented by general formulas (I), (II) and (III) as follows:

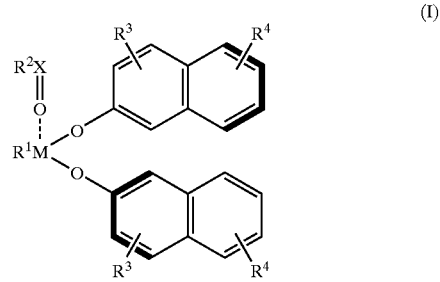

(I)

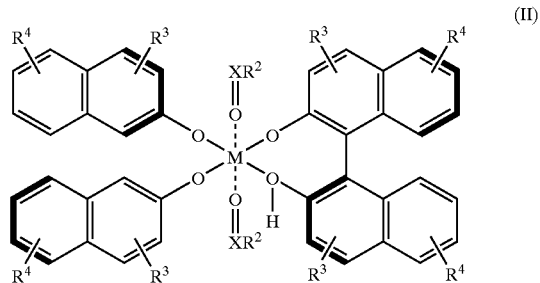

(II)

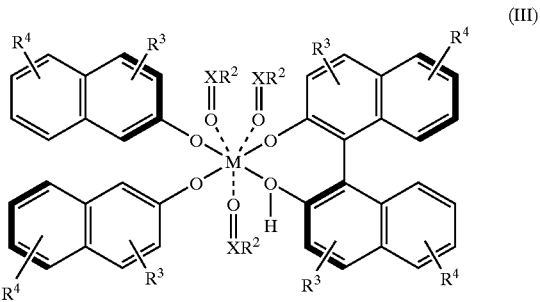

(III)

and wherein X is P or As, and M is a rare earth metal selected from the group consisting of Ce, Pr, Nd, Pm, Sm, Eu, Gd, Dy, Ho, Er and Yb, and $R^1$ is an alkoxy group or an alkyl peroxy group, and $R^2$ is a phenyl group or an alkyl group, and each of $R^3$ and $R^4$ is a substituent on an aromatic ring and wherein each of $R^3$ and $R^4$ is independently selected from the group consisting of an alkyl group, an ether, a halogen atom, an amido group and an ester.

2. The method according to claim 1, wherein the unsaturated amide is an α,β-unsaturated active amide having an imidazole or an oxazolidione.

3. The method according to claim 1, wherein the oxidizing agent is selected from the group consisting of t-butyl hydroperoxide, cumene hydroperoxide and trityl hydroperoxide.

4. The method according to claim 1, wherein the reaction is carried out in the presence of a coordinating solvent.

5. The method according to claim 4, wherein the coordinating solvent is selected from the group consisting of tetrahydrofuran, dimethoxyethane and ether.

6. The method according to claim 1, wherein the reaction is further carried out with an alcohol, a metallic amide, a reducing agent or a metallic enolate to obtain an $\alpha,\beta$-epoxy ester, an $\alpha,\beta$-epoxy amide, an $\alpha,\beta$-epoxy aldehyde and a $\gamma,\delta$-epoxy-$\beta$-ketoester.

* * * * *